US010000818B2

(12) United States Patent
Mayra-Makinen et al.

(10) Patent No.: US 10,000,818 B2
(45) Date of Patent: Jun. 19, 2018

(54) PREVENTION AND DIAGNOSIS OF VISCERAL FAT

(71) Applicant: Gut Guide Oy, Halikko (FI)

(72) Inventors: Annika Mayra-Makinen, Helsinki (FI); Eveliina Munukka, Turku (FI)

(73) Assignee: Gut Guide Oy (FI)

( * ) Notice: Subject to any disclaimer, the term of this patent is extended or adjusted under 35 U.S.C. 154(b) by 461 days.

(21) Appl. No.: 14/350,957

(22) PCT Filed: Oct. 12, 2012

(86) PCT No.: PCT/FI2012/050979
§ 371 (c)(1),
(2) Date: Apr. 10, 2014

(87) PCT Pub. No.: WO2013/054002
PCT Pub. Date: Apr. 18, 2013

(65) Prior Publication Data
US 2014/0286920 A1    Sep. 25, 2014

(30) Foreign Application Priority Data

Oct. 12, 2011  (FI) ...................................... 20116008

(51) Int. Cl.
| C12Q 1/68 | (2018.01) |
| A61K 45/06 | (2006.01) |
| A61K 31/702 | (2006.01) |
| A61K 35/745 | (2015.01) |
| A61K 35/747 | (2015.01) |
| A61B 5/00 | (2006.01) |
| A61K 35/744 | (2015.01) |
| A23L 33/135 | (2016.01) |

(52) U.S. Cl.
CPC ............ *C12Q 1/689* (2013.01); *A23L 33/135* (2016.08); *A61B 5/4872* (2013.01); *A61K 31/702* (2013.01); *A61K 35/744* (2013.01); *A61K 35/745* (2013.01); *A61K 35/747* (2013.01); *A61K 45/06* (2013.01); *A23V 2002/00* (2013.01); *A23V 2200/00* (2013.01); *G01N 2800/044* (2013.01); *G01N 2800/52* (2013.01)

(58) Field of Classification Search
None
See application file for complete search history.

(56) References Cited

U.S. PATENT DOCUMENTS

| 2010/0063000 A1 | 3/2010 | Furuyashiki et al. | |
| 2010/0172874 A1* | 7/2010 | Turnbaugh | A61K 35/74 424/93.4 |
| 2016/0281142 A1* | 9/2016 | Czarnecki-Maulden | ................................ C12Q 1/06 |

FOREIGN PATENT DOCUMENTS

| EP | 1974734 A1 | 10/2008 |
| EP | 2308499 A1 | 4/2011 |
| EP | 2351492 A1 | 8/2011 |
| WO | 2004015421 A1 | 2/2004 |
| WO | 2008076696 A2 | 6/2008 |
| WO | 2009/071086 A2 | 6/2009 |
| WO | 2011005756 A1 | 1/2011 |
| WO | WO 2011/022660 | * 2/2011 |

OTHER PUBLICATIONS

Balamurugan et al. "Quantitative differences in intestinal Faecalibacterium prausnitzii in obese Indian children" British Journal of Nutrition (2010), 103, 335-338.*
Chen et al. "Bifidobacterium adolescentis supplementation ameliorates visceral fat accumulation and insulin sensitivity in an experimental model of the metabolic syndrome" British Journal of Nutrition (2012), 107, 1429-1434.*
Remely et al. "Gut microbiota composition correlates with changes in body fat content due to weight loss" Beneficial Microbes, 2015; 6(4): 431-439.*
Maria Carmen Collado et al., "The impact of probiotic on gut health," Current drug metabolism, Jan. 1, 2009, pp. 68-78, XP055094313, Netherlands, Retrieved from the Internet: URL:http://www.ncbi.nlm.nih.gov/pubmed/19149514.
Collado, MC et al., "Distinct composition of gut microbiota during pregnancy in overweight and normal-weight women," American Journal of Clinical Nutrition, vol. 88, No. 4, Oct. 2008, pp. 894-899, XP055148945.
Backhed, Fedrik et al. The gut microbiota as an environmental factor that regulates fat storage. PNAS, vol. 101 No. 44 15718-15723 (2004).
Cani, Patrice D. et al. Selective increases of bifidobacteria in gut microflora improve high-fat-diet-induced diabetes in mice through a mechanism associated with endotoxaemia. Diabetologia 50:2374-2383 (2007).
Cani, Patrice D. et al. Changes in Gut Microbiota Control Metabolic Endotoxemia-Induced Inflammation in High-Fat Diet-Induced Obesity and Diabetes in Mice. Diabetes, vol. 57 (2008).
Collado, Maria Carmen et al. Distinct composition of gut microbiota during pregnancy in overweight and normal-weight women. Am J Clin Nutr 88:894-899, (2008).
Desbonnet, Lieve et al. The probiotic Bifidobacteria infantis: An assessment of potential antidepressant properties in the rat. Journal of Psychiatric Research 43, 164-174 (2009).

(Continued)

*Primary Examiner* — Thane Underdahl
(74) *Attorney, Agent, or Firm* — Banner & Witcoff, Ltd.

(57) ABSTRACT

The invention is based on a correlation observed between visceral fat and gut flora. The invention relates to a product increasing the relative proportion of *bifidobacteria* in the intestines and to be used for preventing formation of visceral fat or for reducing the amount thereof in the body. In particular, the product increases the ratio of *bifidobacteria* to *Clostridia*. The invention also relates to determining visceral fat in the body by determining the relative proportion of *bifidobacteria* or *Clostridia* or their ratio to each other in the intestines. The invention further relates to a method for estimating, in the same manner, the health risk associated with obesity.

3 Claims, No Drawings

(56) References Cited

OTHER PUBLICATIONS

Franks, Alison H. et al. Variations of Bacterial Population in Human Feces Measured by Fluorescent In Situs Hybridization with Group-Specific 16S rRNA-Targeted Oligonucleotide Probes. Applied and Environmental Microbiology, vol. 64, No. 9, p. 3336-3345, (1998).

Hooper, Lora V. et al. Comnensal Host-Bacterial Relationships in the Gut. Science 292, 1115 (2001).

Ilmonen, Johanna et al. Impact of dietary counselling and probiotic intervention on maternal anthropometric measurements during and after pregnancy: A randomized placebo-controlled trial. Clinical Nutrition 30, 156-164 (2011).

Kadooka, Y. et al. Regulations of abdominal adiposity by probiotics (lactobacillus gasseri SBT2055) in adults with obese tendencies in a randomized controlled trial. European Journal of Clinical Nutrition 64, 636-643 (2010).

Kalliomaki, Marko et al. Early differences in fecal microbiota composition in children may predict overweight. Am J Clinic Nutr 87:534-8 (2008).

Ley, Ruth E. et al. Obesity alters gut microbial ecology. PNAS vol. 102 No. 31 11070-11075 (2005).

Ley, Ruth E. et al. Human gut microbes associated with obesity. Nature vol. 444 21/28 (2006).

Russell, D. A. et al. Metabolic activities and probiotic potential of bifidobacteria. International Journal of Food Microbiology 149 88-105 (2011). El.

Turnbaugh Peter J. et al. An obesity-associated gut microbiome with increased capacity for energy harvest. Nature, vol. 444 21/28 (2006).

Turnbaugh Peter J. et al. A core gut microbiome in obese and lean twins. Nature 457 (7228): 480-484 (2009).

Vaahtovuo, Jussi et al. Quantification of bacteria in human feces using 16S rRna-hybridization, DNA-staining and flow cytometry. Journal of Microbiological Methods 63: 276-286, (2005).

* cited by examiner

PREVENTION AND DIAGNOSIS OF VISCERAL FAT

RELATED APPLICATION DATA

This application is a National Stage Application under 35 U.S.C. 371 of co-pending PCT application PCT/FI2012/050979 designating the United States and filed Oct. 12, 2012; which claims the benefit of FI application number 20116008 and filed Oct. 12, 2011 each of which are hereby incorporated by reference in their entireties.

FIELD OF THE INVENTION

The present invention relates to visceral fat and to the health risk associated therewith. More precisely, the invention relates to a product to be used for preventing and reducing visceral fat formation in the body. The invention also relates to a method for determining visceral fat in the body and for estimating the health risk associated with an obesity-related disease.

BACKGROUND OF THE INVENTION

Overweight and the related diseases have increased over the past few decades like an epidemic in all western countries. What is particularly worrying is an increase in obesity in children and young people.

The obesity epidemic is partly explained by the imbalance between energy intake and energy consumption in the present-day society; in other words, we get more calories from the food that we eat than we consume. The reasons for becoming overweight are diverse: the diet and the small amount of exercise are essential factors, but partially overweight has been regarded as hereditary whereas in some cases it has been related to disorders of hormonal action and to some diseases. Over the past few years, the possible role of gut microbiota in the pathogenesis of obesity has been researched (Bäckhed F, et al. *Proc Natl Acad Sci USA*. 2004; 101:15718-15723).

The composition of gut microbiota has been demonstrated to have numerous effects on the wellbeing and health of the host (Hooper L. V., Gordon J. I., *Science* 2001; 292: 1115-8; and Bäckhed, F. et al. 2005. *Science* 307, 1915-1920). It has been proven that in both test animals and humans there are differences in the microbiota composition of normal and overweight individuals and that the gut microbiota has an effect on the nutrient supply and energy regulation of the host (Backhed F et al. *Proc Natl Acad Sci USA*. 2004; 101: 15718-15723, Ley R E et al. *Proc Natl Acad Sci USA*. 2005; 102: 11070-11075, Ley R E et al. *Nature* 2006; 444: 1022-1023, Cani P D et al., *Diabetes* 2008; 57: 1470-1481, Turnbaugh P J et al. *Nature* 2006; 444: 1027-1031, and Turnbaugh P J et al. *Nature* 2009; 457: 480-484). On the basis of these research results, it can be assumed that gut microbes are significant to weight control and development of overweight. Thus, modifying gut microbiota could, in the future, be a novel method for preventing and treating overweight, and it would naturally also be significant to public health.

Rats were fed on *bifidobacteria*, the effect of which on their weight was monitored. The results were conflicting in the sense that after the first week, the weight gain of the rats having received *bifidobacteria* was smaller than that of the control rats but after another week it was greater (Desbonnet L et al. *J Psychiatr Res*. 2008; 43: 164-174). A disadvantage of animal testing is that the results are not directly applicable to humans. Use of probiotic bacteria has, however, been suggested for promoting development of early bifidogenic gut microbiota in order to reduce the risk of overweight or obesity in small children later in life (EP 1 974 734).

A weak point in studies in the field is usually that they focus on the body weight or, with humans, possibly on the body mass index (BMI), which is the body mass (kg) divided by the square of the height (m). These are, however, unreliable in the estimation of obesity-related health risks. Obesity or overweight harmful to the health of humans and most animals is not dependent on the body weight but on the amount of fat. There is adipose tissue under the skin, around internal organs and in bone marrow, muscles and breast tissue. The fat around internal organs is called visceral fat, and it differs from both subcutaneous fat and fat in muscles. There is visceral fat in the abdominal cavity, for example around the abdomen, liver, intestines and kidneys. It is known that excessive visceral fat correlates intensely with many serious diseases whereas subcutaneous fat does not. It has even been suggested that subcutaneous fat might have a protective effect.

It becomes apparent from the above that when looking for obesity-preventing products, it is desirable to find products that affect specifically visceral fat. Conventionally, formation of visceral fat has been attacked by diet and exercise. The present invention now provides a novel manner for avoiding visceral fat and the related health risk. Visceral fat is usually determined by magnetic resonance imaging (MRI), which requires both special equipment and special know-how. The present invention now provides a simpler and less expensive manner for determining it.

BRIEF DESCRIPTION OF THE INVENTION

The invention is based on the finding that the relative proportion of *bifidobacteria* in the intestines correlates negatively with visceral fat. In particular, it was noted that the ratio of *bifidobacteria* to *clostridia* correlates negatively to visceral fat, whereas the relative proportion of *clostridia* in the intestines correlates positively with visceral fat. Further, the invention is based on the finding that the ratio of the total amount of *bifidobacteria* and *F. prausnitzii*, which are included in the normal flora in the intestines, to the amount of non-pathogenic *clostridia* in the intestines correlates negatively with the amount of visceral fat. The above correlations enable diagnostic methods for determining visceral fat or for estimating the obesity-related health risk by determining the relative proportion of *bifidobacteria* to *clostridia*, or their ratio to each other in the intestines.

The invention relates to a product which increases the relative proportion of *bifidobacteria* in the intestines and is to be used for preventing formation of visceral fat or for reducing the amount thereof in the body. The invention also relates to a product which increases the ratio of *bifidobacteria* to *clostridia* in the intestines and is to be used for preventing formation of visceral fat or for reducing the amount thereof in the body. The invention particularly relates to a product which increases the ratio of the total amount of *bifidobacteria* and *F. prausnitzii* to non-pathogenic *clostridia* in the intestines and is to be used for preventing formation of visceral fat or for reducing the amount thereof in the body.

The invention further relates to a method for determining visceral fat in the body, the method comprising determining in vitro the relative proportion of *bifidobacteria* in the intestines, whereby the relative proportion of *bifidobacteria* in the intestines correlates negatively with visceral fat. The invention also relates to a method for determining visceral fat in the body, comprising determining in vitro the ratio of *bifidobacteria* to *clostridia* in the intestines, whereby the ratio of *bifidobacteria* to *clostridia* correlates negatively with visceral fat. Particularly, the invention relates to a method for determining visceral fat in the body, comprising determining in vitro the ratio of the total amount of *bifidobacteria* and *F. prausnitzii* to *clostridia* in the intestines, whereby the ratio of the total amount of *bifidobacteria* and *F. prausnitzii* to *clostridia* correlates negatively with visceral fat. The invention further relates to a method for determining visceral fat in the body, the method comprising determining in vitro the relative proportion of *clostridia* in the intestines, whereby the relative proportion of *clostridia* in the intestines correlates positively with visceral fat.

The invention further relates to a method for estimating the health risk associated with obesity, the method comprising determining in vitro the relative proportion of *bifidobacteria* in the intestines, whereby the proportion of *bifidobacteria* correlates negatively with the health risk. The invention further relates to a method for estimating the health risk associated with obesity, the method comprising determining in vitro the ratio of *bifidobacteria* to *clostridia* in the intestines, whereby the ratio correlates negatively with the health risk. Furthermore, the invention relates to a method for estimating the health risk associated with obesity, the method comprising determining in vitro the relative proportion of *clostridia* in the intestines, whereby the relative proportion of *clostridia* correlates positively with the health risk.

Further, a method is disclosed for preventing formation of visceral fat and for reducing the amount thereof in the body, the method comprising administering an effective amount of a product that increases the relative proportion of *bifidobacteria* in the intestines to a subject in need of such treatment.

Preferred embodiments of the invention are disclosed in the dependent claims.

One of the advantages of the product used in accordance with the invention is that it is natural and safe. An advantage of the methods according to the invention is that they can be easily implemented without expensive devices or special know-how.

DETAILED DESCRIPTION OF THE INVENTION

"The relative proportion of *bifidobacteria*" refers to the ratio of *bifidobacteria* to other bacteria in the intestines, normally to the total bacteria and particularly to *clostridia*. The product according to the invention, to be used for preventing or reducing formation of visceral fat, is capable of increasing the relative proportion of *bifidobacteria* in the total bacteria in the intestines. In particular, it is capable of increasing the ratio of *bifidobacteria* to *clostridia* in the intestines. Even more particularly, it is capable of increasing the ratio of the total amount of *bifidobacteria* and *F. prausnitzii* to *clostridia* in the intestines. It may also have a decreasing effect on the relative proportion of *clostridia* to the total bacteria in the intestines.

The product increasing the relative proportion of *bidifobacteria* in the intestines may be selected from a group consisting of *bifidobacteria*, prebiotics, *bifidobacteria*+prebiotics, a product stimulating *bifidobacteria*, and any combination of these. *Bifidobacteria* are preferably selected from strains used as probiotics, such as *Bifidobacterium longum, Bifidobacterium bifidum, Bifidobacterium breve* and *Bifidobacterium infantis* and, for example, strains *Bifidobacterium animalis* subsp. *lactis* Bb-12 and *Bifidobacterium lactis* B1. "A probiotic" is a microbe or a component thereof that has a positive effect on the health of the host. Usually it is a live microbe. "A prebiotic" is a component which is usually a carbohydrate (an oligo- or polysaccharide) and which has a selective promoting effect on the growth or activity of one or more bacterial strains in the colon. A prebiotic is preferably a fructo- or galacto-oligosaccharide, fibre, particularly cereal fibre, such as b-glucan of oat, poly-dextrose, special sugar, such as isomaltulose, or for example a fatty acid, such as omega-3 fatty acid, or any mixture of these. The product increasing the relative proportion of *bifidobacteria* preferably contains both *bifidobacteria* and prebiotics. The product stimulating *bifidobacteria* may be a product containing propionic acid bacteria, such as *Propionibacterium freudenreichii, Propionibacterium shermanii*, and/or *lactobasilli*, such as *Lactobacillus acidophilus, Lactobacillus rhamnosus, Lactobacillus casei* or *Lactobacillus lactis*.

According to an embodiment, the product of the invention is of the type increasing the ratio of the total amount of *bifidobacteria* and *F. prausnitzii* to *clostridia* in the intestines, such as lactic acid bacteria shown to inhibit the growth of *clostridia*, such as *lactobacilli*, for example certain *Lactobacillus rhamnosus* and *Lactobacillus casei* strains.

The above-described bacteria and/or prebiotics and/or other active substances affecting the gut flora may be administered mixed in food or drink, for example, or separately in the form of a capsule, granulate, powder or liquid, for example. In other words, the product described here may be in the form of a food, drink, capsule, granulate, powder or liquid containing substances acting on the gut flora. "An effective amount" of a product acting on the gut flora refers to an amount sufficient for changing the relative proportion of *bifidobacteria* or *clostridia* in the intestines and, in particular, the ratio of *bifidobacteria* to *clostridia*.

The above product may be used for preventing formation of visceral fat or for reducing the amount thereof in the body. In this way, health risks or cosmetic handicaps related to visceral fat can be prevented or reduced. In this context, "visceral fat" means adipose tissue formed on surfaces of internal organs in the abdominal cavity. The most reliable way to determine it is MRI. Thus, the product preventing formation of visceral fat or reducing the amount thereof can be used for preventing diseases related particularly to visceral fat, such as for preventing or treating metabolic syndrome, adult-onset diabetes or arterial hypertension.

The amount of visceral fat in the body and the obesity-related health risk are determined indirectly by analysing the microbiota in the body. More specifically, the relative proportion of *bifidobacteria* or *clostridia* in the intestines can be determined from the total bacteria in the intestines and, in particular, the ratio of *bifidobacteria* to *clostridia* is determined. This ratio is here referred to as the "MOODindex" and it is obtained by dividing the relative proportion of *bifidobacteria* by the relative proportion of *clostridia*. The MOODindex produces the best correlations.

The expression "correlates negatively" means that when one variable increases, another one decreases, while "correlates positively" means that when one variable increases, another one increases as well, and vice versa. Thus, the higher the relative proportion of *bifidobacteria* or particularly the MOODindex in a subject is, the less visceral fat he/she has (negative correlation). Correspondingly, the higher the relative proportion of *clostridia*, the more visceral fat there is in the body (positive correlation). Correspondingly, the higher a person's relative proportion of *bifidobac-* teria or particularly his/her MOODindex is, the smaller is his/her risk of getting a disease associated with obesity (negative correlation). Further, the higher a person's relative proportion of *clostridia* is, the higher is his/her risk of getting a disease associated with obesity (positive correlation).

Gut microbiota is an extremely complex ecosystem (50 to 100 species, in total more than $10^{14}$ bacteria). A change in the percentual proportion of one bacteria group for instance during a diet or a probiotic intervention inevitably also changes the percentual proportions of other bacteria groups significant to health. For this reason, it is important to deal not only with the change in individual bacteria groups but also with the change in the whole system. In the present invention, the composition of the bacterial system is represented by a VF index that was observed to be negatively associated with the amount of visceral fat.

The VF index is a simple and understandable parameter representing the composition of gut microbiota. It is calculated from the percentual proportions of three bacteria groups and genera significant to health, i.e. by dividing the sum of the amount of *bifidobacteria* and *F. prausnitzii* in a sample by the amount of *clostridia* XIVa. Balance between these three bacteria groups is important with respect to health and wellbeing. The VF index can be used for representing a favourable change in the composition of the gut bacteria for instance when a person is slimming.

By means of the VF index, a customized probiotic and/or prebiotic intervention aiming at reducing the amount of visceral fat and slimming can be planned for the person. In an embodiment of this invention, the value 2.9 of the VF index represents a phenotype with a low visceral fat area (VFA), and the value 1.5, in turn, represents a phenotype with a large amount of visceral fat.

Normally a fecal sample of the subject is examined to quantitatively determine the *bifidobacteria, clostridia* and/or total bacteria by methods known per se. *Bifidobacteria* and *clostridia* are well known, taxonomically identifiable bacteria groups. "*Bifidobacteria*" are gram-positive, immobile anaerobic bacteria that appear in the digestive tract (and belong to the Bifidobacteriaceae family and particularly to the *Bifidobacterium* genus). "*Clostridia*" are spore-forming, gram-positive anaerobic bacteria (belonging to the *Clostridia* class), which includes *Clostridium* and *Eubacterium* genera, for example. In the context of the invention, *clostridia* are particularly *clostridia* included in the normal flora and belonging to the non-pathogenic *clostridia* group XIVa. *F. prausnitzii* is included in the normal gut microbiota in a healthy adult as one of the most numerous representatives of this microbiota. Preferably, the proportion of *bifidobacteria, F. prausnitzii* and/or *clostridia* in the total bacteria and/or the ratio of *bifidobacteria* to *clostridia* is determined by a method based on 16S rRNA hybridisation, DNA staining and flow cytometry (FCM-FISH), which allows different gut bacteria groups to be determined rapidly and reliably.

"A subject" in this context refers to an animal, particularly a mammal, including man. Preferably the subject is a person.

Example 1

Research Material and Methods

Fecal samples were collected from 57 Finnish basically healthy adults (19 men, 38 women). The samples were stored frozen and the bacteria were isolated from them using the method described previously (Vaahtovuo J et al. *J Microbiol Methods*. 2005; 63:276-286). The bacteria were fixed and the amounts of total bacteria (number per gram of dry matter) were determined from the samples, and also, the following six bacteria groups or genera significant to health and wellbeing were determined from them: *bifidobacteria, Bacteroides*, enteric group, *Atopobium, Faecalibacterium prausnitzii* and *Clostridium* XIVa, which means a cluster of *clostridia* XIVa, i.e. also known as the Erec group (Franks et al. 1998, *Appl. Environ. Microbiol.* 64: 3336-3345). All of the above bacteria groups are, in the light of present knowledge, part of what is called normal microbiota in a human. The determination was made using a patented method based on 16 S rRNA hybridisation, DNA staining and flow cytometry (FCM-FISH) (Vaahtovuo J et al. 2005 supra and WO2004/015421). In addition, the dry matter percentage of the samples was determined.

The body compositions of the test persons were determined by a method based on bioimpedance and by MRI, in which the surface area of visceral fat in the abdominal area is calculated from an image by computer tomography. The test persons filled in questionnaires on their way of life, medical history and medications, if any, and on physical activity. They also kept a food diary for three days. The fecal samples of two test persons had to be discarded from the material due to chronic bowel diseases.

Correlations between different variables were determined by using Pearson's correlation factor.

Results

Table 1 shows the basic data determined on the test persons in the study. In table 1 the test persons are grouped according to gender. Men were older and naturally also heavier than women. In contrast, the women had a higher fat percentage than the men.

TABLE 1

Basic data on the test persons (average, SD in parentheses)

| | Men | Women | T test |
|---|---|---|---|
| Age | 52 (4) | 36 (6) | ***, p = 0.001 |
| Weight (kg) | 84 (12) | 69 (13) | ***, p < 0.001 |
| Waistline (cm) | 97 (10) | 84 (13) | ***, p < 0.001 |
| BMI (kg/m$^2$) | 27.1 (4.1) | 24.7 (4.6) | p = 0.066 |
| Fat percentage | 28 (7) | 36 (10) | ***, p = 0.002 |
| Blood pressure (mmHg) | 135/80 (12/9) | 127/77 (16/10) | p = 0.051/0.208 |

Table 2 shows the average values for dry matter content in feces as well as the relative proportions of different bacteria groups determined by FCM-FISH.

TABLE 2

Analyses of fecal samples (average, SD in parentheses)

| | Men | Women | T test |
|---|---|---|---|
| Dry matter in feces (%) | 24 (7) | 27 (8) | p = 0.189 |
| *Bifidobacteria* (%) | 4.4 (2.9) | 5.6 (5.3) | p = 0.915 |
| *Bacteroides* (%) | 3.6 (2.6) | 2.9 (1.2) | p = 0.352 |
| Enteric group (%) | 0.4 (0.2) | 0.8 (1.3) | ***, p = 0.007 |
| *Atopobium* (%) | 3.7 (2.3) | 3.5 (17) | p = 0.826 |
| *F. prausnitzii* (%) | 10.1 (4.8) | 6.9 (4.1) | *, p = 0.012 |
| *Clostridium* XIVa | 12.4 (8.7) | 8.5 (7.7) | p = 0.054 |

In the study, it was observed that visceral fat correlates positively with the relative proportion of the *Clostridium*

XIVa group (p=0.002), while a clear negative trend was observed with the relative proportion of *bifidobacteria* (p=0.098). In addition, what is called a MOODindex was calculated for each sample, i.e. the relative proportion of *bifidobacteria* was divided by the relative proportion of *clostridia* (*Clostridium* XIVa). Between the MOODindex and visceral fat the correlation was negative (p=0.002). The results are shown in Table 3.

TABLE 3

Correlations, the entire material

| | Bifidobacteria (%) | Clostridium XIVa (%) | MOODindex |
|---|---|---|---|
| Visceral Fat (%) | neg. r, p = 0.098 | mod. pos. r, p = 0.002** | mod. neg. r, p = 0.002** |

Age and gender may affect the results. Statistical analyses were also carried out on a material consisting only of women (n=38, Table 2). In the material consisting only of women, visceral fat correlated negatively with the MOODindex (p=0.011) and almost significantly with *bifidobacteria* (p=0.066). A positive, significant correlation was observed between the *Clostridium* XIVa group and visceral fat (p=0.033). The results are shown in Table 4.

TABLE 4

Correlations, women

| | Bifidobacteria (%) | Clostridium XIVa (%) | MOODindex |
|---|---|---|---|
| Visceral Fat (%) | mod. neg. p = 0.066* | mod. pos. r, p = 0.033* | mod. neg. r, p = 0.011* |

Example 2. Visceral Fat Index (VF Index)

From the research material described in Example 1, the amounts of total bacteria (number/g of dry matter in feces) and the proportions of certain gut bacteria groups and genera (% of total bacteria) were determined with the method described in Example 1.

The material was divided into tertiles with respect to the visceral fat area (VFA):
Group I (<33.3%)
Group II (>33.3% and <66.6%)
Group III (>66.6%)

From the microbiota results, what is called a visceral fat index (VFI) was calculated by dividing the sum of the amount of *bifidobacteria* and *F. prausnitzii* in a sample by the amount of *clostridium* XIVa. The VF index was calculated for each sample from the relative (%) proportions. The results are shown in Table 5.

TABLE 5

Amounts of total bacteria (g/dry matter), and percentages and amounts of different bacteria groups and genera

| | Group I, VFA < 49.2 cm² | Group II, 49.2 cm² VFA < 91.1 cm² | Group III, VFA > 91.1 cm² | P I vs III |
|---|---|---|---|---|
| Total bacteria | 2.8 · 10¹¹ | 2.0 · 10¹¹ | 2.5 · 10¹¹ | 0.461 |
| Bifidobacterium (%) | 5.8 | 5.8 | 4.0 | 0.487 |
| Clostridium XIV a (%) | 5.9 | 10.1 | 13.9 | 0.021 |
| F. prausnitzii (%) | 6.0 | 8.6 | 8.2 | 0.100 |
| Bididobacterium | 1.5 · 10¹⁰ | 1.3 · 10¹⁰ | 1.1 · 10¹⁰ | 0.750 |
| Clostridium XIVa | 1.5 · 10¹⁰ | 2.0 · 10¹⁰ | 3.2 · 10¹⁰ | 0.001 |
| VF Index* | 2.9 | 2.0 | 1.5 | 0.071 |

*The index was calculated for each sample, i.e. the figure in the column is the average of the indices of all samples of the group.
The P value between groups I and III was calculated by using Student's T test.

A statistically significant difference between group III (high VFA) and group 1 (low VFA) in both the relative proportions and the amounts of *clostridium* XIVa as well as a trend in the VF index were observed in the study. Thus, on the basis of this material, the compositions of the gut microbiota in persons with a high and a low VFA, respectively, differ from each other.

The correlations between the amount of visceral fat (Visceral Fat Area, VFA) and the bacteria results (percentages and index) were calculated from the whole material by using Pearson's correlation factor (Table 6).

TABLE 6

The correlations between the amount of visceral fat (Visceral Fat Area, VFA) and the bacteria results (percentages and VF index)

| | Visceral fat (VFA) | p value |
|---|---|---|
| Total bacteria | 0.238 | 0.157 |
| Bifidos (%) | 0.249 | 0.099 |
| Clostridium XIVa (%) | 0.515 | <0.001 |
| F. prausnitzii (%) | 0.268 | 0.079 |
| VF index | 0.395 | 0008 |

A significant, negative correlation (**, 0.008) was observed between the amount of visceral fat (VFA) and the VF index in this material. Between the *clostridium* XIVa group there was a moderate positive correlation (**, <0.001).

Example 3. Intervention

Five healthy, slightly overweight or overweight Finnish women participated in an intervention where the composition of their gut microbiota was analysed before and after a probiotic (Cell Biotech) and/or prebiotic (glucomannan) intervention.

The probiotic powder used in the study contained >1.0*10^9 live bacteria/g. The probiotic powder consists of strains *Lactobacillus rhamnosus, Bifidobacterium breve ja Bifidobacterium infantis*.

During the test, the test persons had one bag (1 g) of probiotic powder a day, mixed in, for example, yoghurt, sour whole milk (viili), quark or cold liquid. The dose of glucomannan was 3 g a day (3×1 g) as capsules. Table 7 shows the results of the intervention.

TABLE 7

| Person | Bifidos (%) | | Clostridium XIVa (%) | | F. prausnitzii | | VF index | |
|---|---|---|---|---|---|---|---|---|
| | Pre | Post | Pre | Post | Pre | Post | Pre | Post |
| I | 6.5 | 1.8 | 6.8 | 15.9 | 7.0 | 4.4 | 2.0 | 0.4 |
| II | 8.3 | 4.5 | 18.8 | 10.3 | 7.7 | 14.4 | 0.85 | 1.8 |
| III | 4.8 | 5.8 | 6.2 | 5.8 | 11.7 | 11.4 | 2.7 | 3.0 |
| IV | 12.7 | 9.1 | 33.3 | 22.6 | 12.4 | 5.6 | 0.75 | 0.65 |
| V | 1.7 | 13.4 | 22.0 | 13.4 | 10.2 | 5.0 | 0.54 | 1.4 |

The VF indices of two test persons (II and V) increased a lot during the test period. Both participated in the probiotic intervention. By contrast, the VF index of person I decreased during the probiotic intervention. Person I reported having had a low-carbohydrate diet for a few days before giving the Post sample. Such a heavy form of diet presumably affected the results. Test person III shows a slight increase in the index. On the other hand, the index was on a good level (2.7) already in the initial situation. The VF index of test person IV remained practically the same for the whole of the study period. The person suffered from inexplicable stomach upsets during the study period. Test persons I, II and V had only probiotic while III and IV had probiotic+glucomannan.

It was observed in the study that there was a connection between the composition of the gut microbiota and the amount of visceral fat. Further, it can be noted that the probiotic intervention described in the study allows the composition of the gut microbiota and through that also the visceral fat in the body to be affected.

It will be apparent to a person skilled in the art that as technology advances, the basic idea of the invention may be implemented in many different ways. The invention and its embodiments are thus not restricted to the examples described above but may vary within the scope of the claims.

The invention claimed is:

1. A method for determining visceral fat area in the body, comprising:
    a) determining in vitro the percentual proportions of *bifidobacteria*, *F. prausnitzii*, and *clostridia* in the intestines, wherein the determining is based on 16S rRNA hybridization, DNA staining and flow cytometry,
    b) calculating a ratio by dividing of the sum of the percentual proportions of *bifidobacteria* and *F. prausnitzii* by the percentual proportion of *clostridia*, and
    c) determining the visceral fat area in the body from the calculated ratio wherein the ratio of >2 represents a phenotype with a lower visceral fat area, than a ratio <2 which represents a phenotype with a higher visceral fat area.

2. The method according to claim 1, wherein the *clostridia* are non-pathogenic *clostridia* of the group XIVa.

3. The method according to claim 1, comprising determining in vitro the percentual proportions of *bifidobacteria*, *F. prausnitzii*, and *clostridia* in fecal microbiota, calculating a ratio by dividing of the sum of the percentual proportions of *bifidobacteria* and *F. prausnitzii* by the percentual proportion of *clostridia*, and further determining the health risk associated with obesity on the basis of the calculated ratio such that wherein the higher the ratio the lower the health risk.

* * * * *